(12) United States Patent
Hagihara et al.

(10) Patent No.: US 10,519,478 B2
(45) Date of Patent: *Dec. 31, 2019

(54) METHOD OF PRODUCING SUBSTANCE

(71) Applicant: UBE INDUSTRIES, LTD., Ube-shi, Yamaguchi (JP)

(72) Inventors: Masahiko Hagihara, Ube (JP); Motohisa Shimizu, Ube (JP); Yukinori Wada, Ube (JP)

(73) Assignee: UBE INDUSTRIES, LTD., Yamaguchi (JP)

(*) Notice: Subject to any disclaimer, the term of this patent is extended or adjusted under 35 U.S.C. 154(b) by 0 days.

This patent is subject to a terminal disclaimer.

(21) Appl. No.: 15/545,624

(22) PCT Filed: Jan. 26, 2016

(86) PCT No.: PCT/JP2016/052207
§ 371 (c)(1),
(2) Date: Jan. 11, 2018

(87) PCT Pub. No.: WO2016/121768
PCT Pub. Date: Aug. 4, 2016

(65) Prior Publication Data
US 2018/0016611 A1    Jan. 18, 2018

(30) Foreign Application Priority Data

Jan. 26, 2015  (JP) .................... 2015-012834

(51) Int. Cl.
| | |
|---|---|
| *C12P 21/00* | (2006.01) |
| *C12N 7/00* | (2006.01) |
| *C12P 1/00* | (2006.01) |
| *C12M 1/12* | (2006.01) |
| *C12N 5/00* | (2006.01) |

(52) U.S. Cl.
CPC ............ *C12P 21/00* (2013.01); *C12M 25/00* (2013.01); *C12M 25/02* (2013.01); *C12N 5/0068* (2013.01); *C12N 7/00* (2013.01); *C12P 1/00* (2013.01); *C12N 2533/30* (2013.01); *C12N 2535/00* (2013.01)

(58) Field of Classification Search
CPC ... C12P 21/00; C12N 5/0068; C12N 2535/00; C12N 2533/30; C12M 25/00
See application file for complete search history.

(56) References Cited

U.S. PATENT DOCUMENTS

| | | | | |
|---|---|---|---|---|
| 4,228,243 A * | 10/1980 | Iizuka | ................ | C12M 23/34 |
| | | | | 435/294.1 |
| 5,378,612 A | 1/1995 | Nakashima et al. | | |
| 6,900,052 B1 | 5/2005 | Ozaki et al. | | |
| 2003/0108860 A1 | 6/2003 | Reiter et al. | | |
| 2011/0290112 A1* | 12/2011 | Liu | ................ | B01D 53/228 |
| | | | | 95/54 |
| 2011/0318556 A1* | 12/2011 | Ohya | ................ | C08J 9/28 |
| | | | | 428/216 |
| 2012/0207999 A1* | 8/2012 | Ohya | ................ | C08J 5/18 |
| | | | | 428/220 |

FOREIGN PATENT DOCUMENTS

| | | | |
|---|---|---|---|
| JP | 63-196286 A | | 8/1988 |
| JP | 63196286 | * | 8/1988 |
| JP | 06-030570 B | | 4/1994 |
| JP | H0630570 B2 | | 4/1994 |
| JP | 2683946 B2 | | 12/1997 |
| JP | 2009-261410 A | | 11/2009 |
| JP | 2011-219585 A | | 11/2011 |
| JP | 2011-219586 A | | 11/2011 |
| JP | 2011-244713 A | | 12/2011 |
| JP | 2013-215152 A | | 10/2013 |
| JP | 2014-094501 A | | 5/2014 |
| WO | WO-96/10966 A1 | | 4/1996 |
| WO | 00/68371 A1 | | 11/2000 |
| WO | 03/054174 A1 | | 7/2003 |
| WO | 2010-038873 A1 | | 4/2010 |
| WO | 2015/012415 A1 | | 1/2015 |

OTHER PUBLICATIONS

H. Ahern. The Scientist Magazine, Feb 1990, 2 pages. "Hollow Fiber Bioreactor Systems Increase Cell Culture Yield". (Year: 1990).*
Kim et al. CHO cells in biotechnology for production of recombinant proteins: current state and further potential. Appl. Microbiol. Biotechnol. (2012), v93, p. 917-930. (Year: 2012).*
Inloes et al. Hollow-Fiber Membrane Bioreactors Using Immobilized *E. coli* for Protein Synthesis.Biotechnology and Bioengineering (1983), v25, p. 2653-2681. (Year: 1983).*
International Search Report dated Mar. 29, 2016 corresponding to International Patent Application No. PCT/JP/2016/052207, filed on Jan. 26, 2016; 2 pages.
Julien, Sylvie et al., "Implantation of ultrathin, biofunctionalized polyimide membranes into the subretinal space of rats," *Bomaterials* (Mar. 8, 2011 online); 32:3890-3898.
Hogwood, Catherine EM et al., "Measurement and control of host cell proteins (HCPs) in CHO cell bioprocesses," *Current Opinion in Biotechnology* (Jul. 15, 2014); 30:153-160.
Kurokawa, Masato et al., "Growth and poliovirus production of Vero cells on a novel microcarrier with artificial cell adhesive protein under serum-free conditions," *Journal of Bioscience and Bioengineering* (Jan. 23, 2011); 111(5):600-604.
Tao, Chun-Te et al., "Polyetherimide membrane formation by the cononsolvent system and its biocompatibility of MG63 cell line," *Journal of Membrane Science* (Feb. 1, 2006); 269:66-74.

(Continued)

*Primary Examiner* — Sean C. Barron
(74) *Attorney, Agent, or Firm* — Mintz Levin Cohn Ferris Glovsky and Popeo PC

(57) ABSTRACT

The present invention relates to a method of using cells to produce a substance, and involves applying the cells to a polyimide porous film, culturing the cells and producing the substance by means of the cells.

15 Claims, 1 Drawing Sheet

(56) References Cited

OTHER PUBLICATIONS

Campos, Doris M. et al., "Role of culture conditions on in vitro transformation and cellular colonization of biomimetic HA-Col. scaffolds," *Biomatter* (Accepted May 3, 2013); 3(2):e24922-1-e24922-10; http://dx.doi.org/10.4161/biom.24922.
Guillen, Gregory R. et al., "Preparation and Characterization of Membranes Formed by Nonsolvent Induced Phase Separation: A Review," *Ind. Eng. Chem. Res.* (Mar. 8, 2011); 50:3798-3817.
Jansen, Johannes Carolus et al., "Asymmetric membranes of modified poly(ether ether ketone) with an ultra-thin skin for gas and vapour separations," *Journal of Membrane Science* (2006; available online Sep. 22, 2005); 272:188-197.
Ou, Keng-Liang et al., "Development of 3D in Vitro Technology for Medical Applications," *Int. J. Mol. Sci.* (Oct. 8, 2014) 15:17938-17962.

* cited by examiner

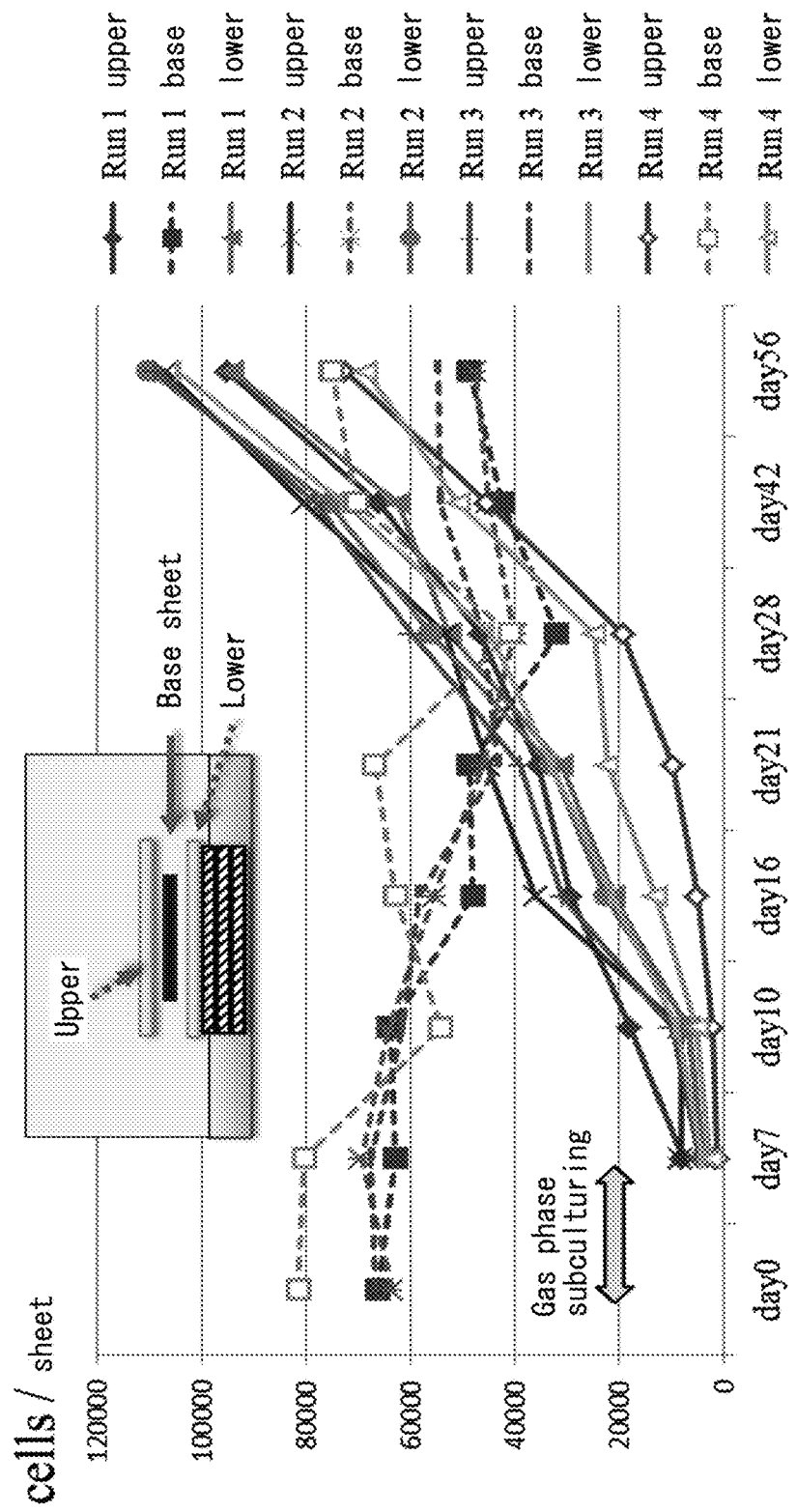

METHOD OF PRODUCING SUBSTANCE

TECHNICAL FIELD

The present invention relates to a method of producing a substance by using cells.

BACKGROUND ART

Cell Culturing and Substance Production

Cells generally exist as three-dimensional aggregates in the body. However, when cells are cultured in an artificial environment, it is common to use the classical plate culture method in which the cells are cultured two-dimensionally in a manner plated as a monolayer on the bottom of the culturing vessel, or a suspension culture method in which cells are cultured while dispersed in a liquid culture solution. Cells most suited for the plate culture method are cells having relatively high adhesion, but even when such suitable cells are used, differences in the culturing environment can often result in significant changes in the properties of the cells. With suspension culture methods as well, certain cells are suitable while others are not.

With increasing demand for in vivo proteins to be used for medical purposes, such as vaccines, enzymes, hormones, antibodies, cytokines and the like, interest is becoming increasingly focused on mass production of such in vivo proteins by cell culturing. For suspended cells of E. coli and the like, research is being conducted on techniques for mass culturing in large-scale culturing tanks. Mass culturing of suspended cells using large-scale culturing tanks requires large volumes of culture solution and an agitating apparatus. Increasing focus is also being directed toward research in which substances are produced using adherent cells, as research on such cells continues to progress. In the case of adherent cells, the cells will only expand two-dimensionally when the classical plate culture method is employed, and therefore a large culturing area is necessary. In order to perform mass production of in vivo proteins, etc., a lot of researches are also being conducted on cell culture carriers and bioreactors for three-dimensional and mass cell culture.

Microcarriers, which are microparticles on which cells can adhere and grow, are being widely studied as typical cell culturing supports (PTL 3). Different types of microcarriers have been studied and developed, and many are available on the market. They are often used for production of vaccines and proteins, and widely employed as methodologies in upscalable systems. In microcarrier culturing, however, the microcarriers must be adequately stirred and diffused to avoid their aggregation, and this places a limit on the cell culture volume. Moreover, for production of a substance, for example, the procedure is methodologically complex as well, since fine particles must be separated with a fractionating filter or the like in order to separate the carrier itself. In addition, since the form of the particulate matter of a microcarrier used in microcarrier culturing is limited, it is impossible to avoid the properties that arise from its form.

Alternative methods to microcarrier culturing have been discovered, such as methods of continuous mass culturing of spheroid cells by three-dimensional culturing using methyl cellulose or gellan gum. It is indeed possible to achieve mass culturing of cells in a bioreactor using a cellulose sponge. Being a large closed system, however, there are many restrictions on its operation, such as the inability to easily contact the culturing environment.

It has been a goal to establish a novel system that is suited for convenience and automation and that allows efficient production of numerous substances in large quantities in cells.

Porous Polyimide Film

The term "polyimide" is a general term for polymers including imide bonds in the repeating unit. An "aromatic polyimide" is a polymer in which aromatic compounds are directly linked by imide bonds. An aromatic polyimide has an aromatic-aromatic conjugated structure via an imide bond, and therefore has a strong rigid molecular structure, and since the imide bonds provide powerful intermolecular force, it has very high levels of thermal, mechanical and chemical properties.

Porous polyimide films have been utilized in the prior art for filters and low permittivity films, and especially for battery-related purposes, such as fuel cell electrolyte membranes and the like. PTLs 6 to 8 describe porous polyimide films with numerous macro-voids, having excellent permeability for gases and the like, high porosity, excellent smoothness on both surfaces, relatively high strength and, despite high porosity, also excellent resistance against compression stress in the film thickness direction. All of these are porous polyimide films formed via amic acid.

CITATION LIST

Patent Literature

[PTL 1] Japanese Examined Patent Publication No. HEI 6-30570
[PTL 2] Japanese Patent No. 2683946
[PTL 3] WO2003/054174
[PTL 4] Japanese Unexamined Patent Publication No. 2009-261410
[PTL 5] WO2000/068371
[PTL 6] WO2010/038873
[PTL 7] Japanese Unexamined Patent Publication No. 2011-219585
[PTL 8] Japanese Unexamined Patent Publication No. 2011-219586

Non-Patent Literature

[NPL 1] Hogwood et al., Current Opinion in Biotechnology 2014, 30:153-160
[NPL 2] Kurokawa et al., Journal of Bioscience and Bioengineering VOL. 111 No. 5, 600-604, 2011

DISCLOSURE OF THE INVENTION

Problems to be Solved by the Invention

It is an object of the present invention to provide a method for producing a substance using cells, a substance-producing apparatus and kit, and use of the same.

Means for Solving the Problems

As a result of diligent research conducted with the aim of providing a method and system that allow convenient and efficient production of substances in cells, the present inventors have completed this invention upon finding that by conducting culturing using a porous polyimide film, it is possible to culture large quantities of cells in a limited space without any special pretreatment, taking advantage of high-density culture characteristics to accomplish efficient substance production. Thus, one feature of the invention is culturing of cells using a porous polyimide film.

Cells grow stably and independently by utilizing the large diameter communicating pores in the porous polyimide film, through which the cells are able to pass, so that even when large quantities of cells are present in comparison to plate culturing, it is possible to ensure contact of the communicating pores with the medium and thereby allow stable growth to be continued. The same structural features also contribute in the production of substances such as proteins and viruses, allowing the produced substances to be efficiently supplied to the medium. Moreover, due to the thin-film properties, flexible properties, form stability and free shapeability of porous polyimide films, it is possible to insert large amounts of sheets in small unit spaces and to layer multiple films, while the high heat resistance and solvent resistance of porous polyimide films allow convenient and rapid sterilization of the sheets to be accomplished by various means. In addition, the three-dimensional scaffold structure of a porous polyimide film offers the possibility of increasing substance productivity per cell, compared to flat culturing.

The present invention preferably includes, but is not limited to, the following modes.

[Mode 1]

A method of producing a substance using cells, the method including applying the cells to a porous polyimide film and culturing the cells to produce the substance by the cells.

[Mode 2]

The method according to mode 1, wherein the substance is selected from the group consisting of proteins, glycoproteins and viruses.

[Mode 3]

The method according to mode 1 or 2, wherein the cells are cultured under stationary culture conditions.

[Mode 4]

The method according to mode 1 or 2, wherein the cells are cultured under rotating culture or stirred conditions.

[Mode 5]

The method according to mode 1 or 2, wherein the cells are cultured in a continuous manner.

[Mode 6]

The method according to mode 5, including:

setting a cell culturing apparatus in an incubator and culturing the cells, wherein the cell culturing apparatus includes:

a culturing unit that houses one or more porous polyimide films to support cells, and that comprises a culture medium supply port and a culture medium discharge port, and a culture medium-supply unit comprising a culture medium housing vessel, a culture medium supply line, and a liquid conveyance pump that conveys the medium through the culture medium supply line, the first end of the culture medium supply line contacting the medium in the culture medium housing vessel, and the second end of the culture medium supply line being in communication with the culturing unit interior via the culture medium supply port of the culturing unit.

[Mode 7]

The method according to mode 6, wherein the cell culturing apparatus does not have an air supply port, an air discharge port and an oxygen permeation film.

[Mode 8]

The method according to any one of modes 1 to 7, wherein the porous polyimide film is a porous polyimide film including a polyimide obtained from a tetracarboxylic dianhydride and a diamine.

[Mode 9]

The method according to mode 8, wherein the porous polyimide film is a colored porous polyimide film obtained by forming a polyamic acid solution composition including a polyamic acid solution obtained from a tetracarboxylic dianhydride and a diamine, and a coloring precursor, and then heat treating it at 250° C. or higher.

[Mode 10]

The method according to mode 8 or 9, wherein the porous polyimide film is a porous polyimide film with a multilayer structure, having two different surface layers and a macrovoid layer.

[Mode 11]

The method according to mode 10, wherein the film thickness of the porous polyimide film is no greater than 75 µm.

[Mode 12]

The method according to any one of modes 1 to 11, wherein the porous polyimide film is:
i) folded,
ii) wound into a roll,
iii) connected as sheets or fragments by a filamentous structure, or
iv) bound into a rope, and suspended or anchored in the cell culture medium in the cell culturing vessel.

[Mode 13]

The method according to any one of modes 1 to 12, using two or more porous polyimide films layered either above and below or left and right in the cell culture medium.

[Mode 14]

The method according to any one of modes 1 to 13, wherein the cells are transformed by genetic engineering technology so as to express a substance.

[Mode 15]

The method according to any one of modes 1 to 14, wherein the cells are selected from the group consisting of animal cells, insect cells, plant cells, yeast cells and bacteria.

[Mode 16]

The method according to mode 15, wherein the animal cells are cells derived from an animal belonging to the subphylum Vertebrata.

[Mode 17]

The method according to mode 15 or 16, wherein the animal cells are selected from the group consisting of Chinese hamster ovary tissue-derived cells (CHO cells), African green monkey kidney-derived established cell lines (Vero cells), human hepatic cancer-derived cells (HepG2 cells), canine kidney epithelial cell-derived cell lines (MDCK cells) and human hepatic cancer tissue-derived established cell lines (huGK-14).

[Mode 18]

The method according to mode 15, wherein the bacteria are selected from the group consisting of lactic acid bacteria, *E. coli, Bacillus subtilis* and cyanobacteria.

[Mode 19]

A substance-producing apparatus for use in the method according to any one of modes 1 to 18, including a porous polyimide film.

[Mode 20]

The substance-producing apparatus according to mode 19, wherein two or more porous polyimide films are layered either above and below or left and right.

[Mode 21]

A kit for use in the method according to any one of modes 1 to 18, including a porous polyimide film.

[Mode 22]

Use of a porous polyimide film in the method according to any one of modes 1 to 18.

Effect of the Invention

The method of the invention, when used to carry out culturing using a porous polyimide film with an apparatus and kit, allows a large volume of cells to be efficiently cultured by placing one or more sheets together in a limited space in various forms. With the method of the invention it has become possible to produce substances by efficient and convenient cell culturing.

BRIEF DESCRIPTION OF THE DRAWINGS

FIG. 1 shows changes in cell counts during gas phase subculturing after long term culturing of human skin fibroblasts.

MODE FOR CARRYING OUT THE INVENTION

I. Method of Producing Substance

The present invention relates to a method of producing a substance using cells. The method of the invention includes applying cells to a porous polyimide film and culturing the cells to produce a substance by the cells.

1. Cells

There are no particular restrictions on the type of cells that can be utilized for the method of the invention, and it may be used for growth of any type of cells.

For example, the cells may be selected from the group consisting of animal cells, insect cells, plant cells, yeast cells and bacteria. Animal cells are largely divided into cells from animals belonging to the subphylum Vertebrata, and cells from non-vertebrates (animals other than animals belonging to the subphylum Vertebrata). There are no particular restrictions on the source of the animal cells, for the purpose of the present specification. Preferably, they are cells from an animal belonging to the subphylum Vertebrata. The subphylum Vertebrata includes the superclass Agnatha and the superclass Gnathostomata, the superclass Gnathostomata including the class Mammalia, the class Aves, the class Amphibia and the class Reptilia. Preferably, they are cells from an animal belonging to the class Mammalia, generally known as mammals. Mammals are not particularly restricted but include, preferably, mice, rats, humans, monkeys, pigs, dogs, sheep and goats.

While not a restriction, the animal cells used are preferably cells selected from the group consisting of Chinese hamster ovary-derived cells (CHO cells), African green monkey kidney-derived established cell lines (Vero cells), human hepatic cancer-derived cells (HepG2 cells), canine kidney epithelial cell-derived cell lines (MDCK cells), human hepatic cancer tissue-derived established cell lines (huGK-14), normal human fibroblast-like synovial membrane cells (HFLS cells) and chronic rheumatoid arthritis patient-derived fibroblast-like synovial membrane cells (HFLS-RA cells).

There are also no particular restrictions on sources of plant cells, for the purpose of the present specification. Suitable cells are from plants including bryophytes, pteridophytes and spermatophytes.

Plants from which spermatophyte cells are derived include both monocotyledons and dicotyledons. While not restrictive, monocotyledons include Orchidaceae plants, Poaceae plants (rice, corn, barley, wheat, sorghum and the like) and Cyperaceae plants. Dicotyledons include plants belonging to many subclasses including the subclass Chrysanthemum, the subclass Magnoliidae and the subclass Rosidae.

Algae may be considered cell-derived organisms. These include different groups, from the eubacteria Cyanobacteria (blue-green algae), to eukaryotic monocellular organisms (diatoms, yellow-green algae, dinoflagellates and the like) and multicellular marine algae (red algae, brown algae and green algae).

There are no particular limitations on the types of archaebacteria or bacteria for the purpose of the present specification. Archaebacteria are composed of groups comprising methanogenic bacteria, extreme halophilic bacteria, thermophilic acidophilic bacteria, hyperthermophilic bacteria and the like. Bacteria are selected from the group consisting of, for example, lactic acid bacteria, *E. coli, Bacillus subtilis* and cyanobacteria.

The types of animal cells or plant cells that may be used for the method of the invention are not particularly restricted, but are preferably selected from the group consisting of pluripotent stem cells, tissue stem cells, somatic cells and germ cells.

The term "pluripotent stem cells", for the purpose of the invention, is intended as a comprehensive term for stem cells having the ability to differentiate into cells of a variety of tissues (pluripotent differentiating power). While not restrictive, pluripotent stem cells include embryonic stem cells (ES cells), induced pluripotent stem cells (iPS cells), embryonic germ cells (EG cells) and germ stem cells (GS cells). They are preferably ES cells or iPS cells. Particularly preferred are iPS cells, which are free of ethical problems, for example. The pluripotent stem cells used may be any publicly known ones, and for example, the pluripotent stem cells described in International Patent Publication No. WO2009/123349 (PCT/JP2009/057041) may be used.

The term "tissue stem cells" refers to stem cells that are cell lines capable of differentiation but only to limited specific tissues, though having the ability to differentiate into a variety of cell types (pluripotent differentiating power). For example, hematopoietic stem cells in the bone marrow are the source of blood cells, while neural stem cells differentiate into neurons. Additional types include hepatic stem cells from which the liver is formed and skin stem cells that form skin tissue. Preferably, the tissue stem cells are selected from among mesenchymal stem cells, hepatic stem cells, pancreatic stem cells, neural stem cells, skin stem cells and hematopoietic stem cells.

The term "somatic cells" refers to cells other than germ cells, among the cells composing a multicellular organism. In sexual reproduction these are not passed on to the next generation. Preferably, the somatic cells are selected from among hepatocytes, pancreatic cells, muscle cells, bone cells, osteoblasts, osteoclasts, chondrocytes, adipocytes, skin cells, fibroblasts, pancreatic cells, renal cells and lung cells, or blood cells such as lymphocytes, erythrocytes, leukocytes, monocytes, macrophages or megakaryocytes.

The term "germ cells" refers to cells having the role of passing on genetic information to the succeeding generation in reproduction. These include, for example, gametes for sexual reproduction, i.e. the ova, egg cells, sperm, sperm cells, and spores for asexual reproduction.

The cells may also be selected from the group consisting of sarcoma cells, established cell lines and transformants. The term "sarcoma" refers to cancer occurring in non-epithelial cell-derived connective tissue cells, such as the bone, cartilage, fat, muscle or blood, and includes soft tissue sarcomas, malignant bone tumors and the like. Sarcoma cells are cells derived from sarcoma. The term "established cell line" refers to cultured cells that are maintained in vitro for long periods and reach a stabilized character and can be semi-permanently subcultured. Cell lines derived from various tissues of various species including humans exist, such as PC12 cells (from rat adrenal medulla), CHO cells (from Chinese hamster ovary), HEK293 cells (from human embryonic kidney), HL-60 cells from (human leukocytes) and HeLa cells (from human cervical cancer), Vero cells (from African green monkey kidney epithelial cells), MDCK cells (from canine renal tubular epithelial cells) and HepG2 cells (from human hepatic cancer). The term "transformants" refers to cells with an altered genetic nature by extracellularly introduced nucleic acid (DNA and the like).

The cells are not particularly restricted so long as they are cells that can exhibit a desired substance. The cells may naturally express the substance, or they may be transformed by genetic engineering technology so as to produce the substance. The cells are preferably cells that have been transformed by genetic engineering technology so as to produce the substance. Suitable methods are known for transformation of animal cells, plant cells and bacteria. (For example, MOLECULAR CLONING: A Laboratory Manual (Fourth Edition), Michael R Green and Joseph Sambrook, 2012, (Cold Spring Harbor Laboratory Press), Mutation Research 760 (2014) 36-45, Reviews in Mutation Research).

2. Substance

The type of substance that can be produced by cells using the method of the invention is not particularly restricted, so long as the substance can be produced in the cells naturally or by genetic engineering technology. Preferably, the substance is one selected from the group consisting of proteins (including polypeptides), glycoproteins and viruses.

Examples of proteins include physiologically active proteins such as erythropoietin, insulin and albumin, cytokines such as tumor necrosis factor $\alpha$, interleukin-6 (IL-6), interleukin-8 (IL-8), granulocyte colony stimulating factor (G-CSF) and interferon, enzymes such as thrombin and trypsin, and monoclonal antibodies containing antibody drugs. Physiologically active proteins and monoclonal antibodies are preferred.

Examples of glycoproteins include collagen, fibronectin and hyaluronic acid. Fibronectin is preferred.

Examples of viruses include influenza virus and adenovirus. Influenza virus is preferred.

Examples of substances naturally expressed in specific cells according to the invention include antibody drugs expressed by transformants, and human collagen or fibronectin expressed by human skin fibroblasts.

3. Porous Polyimide Film

Polyimide is a general term for polymers containing imide bonds in the repeating unit, and usually it refers to an aromatic polyimide in which aromatic compounds are directly linked by imide bonds. An aromatic polyimide has an aromatic-aromatic conjugated structure via an imide bond, and therefore has a strong rigid molecular structure, and since imide bonds have powerful intermolecular force, it has very high levels of thermal, mechanical and chemical properties.

The porous polyimide film used for the invention is preferably a porous polyimide film including (as the main component) a polyimide obtained from a tetracarboxylic dianhydride and a diamine, and more preferably it is a porous polyimide film comprising a polyimide obtained from a tetracarboxylic dianhydride and a diamine. The phrase "including as the main component" means that it essentially contains no components other than the polyimide obtained from a tetracarboxylic dianhydride and a diamine, as constituent components of the porous polyimide film, or that it may contain them but they are additional components that do not affect the properties of the polyimide obtained from the tetracarboxylic dianhydride and diamine.

The porous polyimide film used for the invention also includes colored porous polyimide films obtained by forming a polyamic acid solution composition containing a polyamic acid solution obtained from a tetracarboxylic acid component and a diamine component, and a coloring precursor, and then heat treating it at 250° C. or higher.

Polyamic Acid

A polyamic acid is obtained by polymerization of a tetracarboxylic acid component and a diamine component. A polyamic acid is a polyimide precursor that can be cyclized to a polyimide by thermal imidization or chemical imidization.

The polyamic acid used may be any one that does not have an effect on the invention, even if a portion of the amic acid is imidized. Specifically, the polyamic acid may be partially thermally imidized or chemically imidized.

When the polyamic acid is to be thermally imidized, there may be added to the polyamic acid solution, if necessary, an imidization catalyst, an organic phosphorus-containing compound, or fine particles such as inorganic fine particles or organic fine particles. Also, when the polyamic acid is to be chemically imidized, there may be added to the polyamic acid solution, if necessary, a chemical imidization agent, a dehydrating agent, or fine particles such as inorganic fine particles or organic fine particles. Even if such components are added to the polyamic acid solution, they are preferably added under conditions that do not cause precipitation of the coloring precursor.

Coloring Precursor

A coloring precursor to be used for the invention is a precursor that generates a colored substance by partial or total carbonization under heat treatment at 250° C. or higher.

Coloring precursors to be used for the invention are preferably uniformly dissolved or dispersed in a polyamic acid solution or polyimide solution and subjected to thermal decomposition by heat treatment at 250° C. or higher, preferably 260° C. or higher, even more preferably 280° C. or higher and more preferably 300° C. or higher, and preferably heat treatment in the presence of oxygen such as air, at 250° C., preferably 260° C. or higher, even more preferably 280° C. or higher and more preferably 300° C. or higher, for carbonization to produce a colored substance, more preferably producing a black colored substance, with carbon-based coloring precursors being most preferred.

The coloring precursor, when being heated, first appears as a carbonized compound, but compositionally it contains other elements in addition to carbon, and also includes layered structures, aromatic crosslinked structures and tetrahedron carbon-containing disordered structures.

Carbon-based coloring precursors are not particularly restricted, and for example, they include tar or pitch such as petroleum tar, petroleum pitch, coal tar and coal pitch, coke, polymers obtained from acrylonitrile-containing monomers, ferrocene compounds (ferrocene and ferrocene derivatives), and the like. Of these, polymers obtained from acrylonitrile-containing monomers and/or ferrocene compounds are preferred, with polyacrylnitrile being preferred as a polymer obtained from an acrylonitrile-containing monomer.

The tetracarboxylic dianhydride used may be any tetracarboxylic dianhydride, selected as appropriate according to the properties desired. Specific examples of tetracarboxylic dianhydrides include biphenyltetracarboxylic dianhydrides such as pyromellitic dianhydride, 3,3',4,4'-biphenyltetracarboxylic dianhydride (s-BPDA) and 2,3,3',4'-biphenyltetracarboxylic dianhydride (a-BPDA), oxydiphthalic dianhydride, diphenylsulfone-3,4,3',4'-tetracarboxylic dianhydride, bis(3,4-dicarboxyphenyl)sulfide dianhydride, 2,2-bis(3,4-dicarboxyphenyl)-1,1,1,3,3,3-hexafluoropropane dianhydride, 2,3,3',4'-benzophenonetetracarboxylic dianhydride, 3,3',4,4'-benzophenonetetracarboxylic dianhydride, bis(3,4-dicarboxyphenyl)methane dianhydride, 2,2-bis(3,4-dicarboxyphenyl)propane dianhydride, p-phenylenebis(trimellitic acid monoester acid anhydride), p-biphenylenebis(trimellitic acid monoester acid anhydride), m-terphenyl-3,4,3',4'-tetracarboxylic dianhydride, p-terphenyl-3,4,3',4'-tetracarboxylic dianhydride, 1,3-bis(3,4-dicarboxyphenoxy) benzene dianhydride, 1,4-bis(3,4-dicarboxyphenoxy) benzene dianhydride, 1,4-bis(3,4-dicarboxyphenoxy) biphenyl dianhydride, 2,2-bis[(3,4-dicarboxyphenoxy) phenyl]propane dianhydride, 2,3,6,7-naphthalenetetracarboxylic dianhydride, 1,4,5,8-naphthalenetetracarboxylic dianhydride, 4,4'-(2,2-hexafluoroisopropylidene)diphthalic dianhydride, and the like. Also preferably used is an aromatic tetracarboxylic acid such as 2,3,3',4'-diphenylsulfonetetracarboxylic acid. These may be used alone or in appropriate combinations of two or more.

Particularly preferred among these are at least one type of aromatic tetracarboxylic dianhydride selected from the group consisting of biphenyltetracarboxylic dianhydride and pyromellitic dianhydride. As a biphenyltetracarboxylic dianhydride there may be suitably used 3,3',4,4'-biphenyltetracarboxylic dianhydride.

Any desired diamine may be used as a diamine. Specific examples of diamines include the following.

1) Benzenediamines with one benzene nucleus, such as 1,4-diaminobenzene(paraphenylenediamine), 1,3-diaminobenzene, 2,4-diaminotoluene and 2,6-diaminotoluene;

2) diamines with two benzene nuclei, including diaminodiphenyl ethers such as 4,4'-diaminodiphenyl ether and 3,4'-diaminodiphenyl ether, and 4,4'-diaminodiphenylmethane, 3,3'-dimethyl-4,4'-diaminobiphenyl, 2,2'-dimethyl-4,4'-diaminobiphenyl, 2,2'-bis(trifluoromethyl)-4,4'-diaminobiphenyl, 3,3'-dimethyl-4,4'-diaminodiphenylmethane, 3,3'-dicarboxy-4,4'-diaminodiphenylmethane, 3,3',5,5'-tetramethyl-4,4'-diaminodiphenylmethane, bis(4-aminophenyl)sulfide, 4,4'-diaminobenzanilide, 3,3'-dichlorobenzidine, 3,3'-dimethylbenzidine, 2,2'-dimethylbenzidine, 3,3'-dimethoxybenzidine, 2,2'-dimethoxybenzidine, 3,3'-diaminodiphenyl ether, 3,4'-diaminodiphenyl ether, 4,4'-diaminodiphenyl ether, 3,3'-diaminodiphenyl sulfide, 3,4'-diaminodiphenyl sulfide, 4,4'-diaminodiphenyl sulfide, 3,3'-diaminodiphenylsulfone, 3,4'-diaminodiphenylsulfone, 4,4'-diaminodiphenylsulfone, 3,3'-diaminobenzophenone, 3,3'-diamino-4,4'-dichlorobenzophenone, 3,3'-diamino-4,4'-dimethoxybenzophenone, 3,3'-diaminodiphenylmethane, 3,4'-diaminodiphenylmethane, 4,4'-diaminodiphenylmethane, 2,2-bis(3-aminophenyl)propane, 2,2-bis(4-aminophenyl)propane, 2,2-bis(3-aminophenyl)-1,1,1,3,3,3-hexafluoropropane, 2,2-bis(4-aminophenyl)-1,1,1,3,3,3-hexafluoropropane, 3,3'-diaminodiphenyl sulfoxide, 3,4'-diaminodiphenyl sulfoxide and 4,4'-diaminodiphenyl sulfoxide;

3) diamines with three benzene nuclei, including 1,3-bis(3-aminophenyl)benzene, 1,3-bis(4-aminophenyl)benzene, 1,4-bis(3-aminophenyl)benzene, 1,4-bis(4-aminophenyl)benzene, 1,3-bis(4-aminophenoxy)benzene, 1,4-bis(3-aminophenoxy)benzene, 1,4-bis(4-aminophenoxy)benzene, 1,3-bis(3-aminophenoxy)-4-trifluoromethylbenzene, 3,3'-diamino-4-(4-phenyl)phenoxybenzophenone, 3,3'-diamino-4,4'-di(4-phenylphenoxy) benzophenone, 1,3-bis(3-aminophenyl sulfide)benzene, 1,3-bis(4-aminophenyl sulfide)benzene, 1,4-bis(4-aminophenyl sulfide)benzene, 1,3-bis(3-aminophenylsulfone)benzene, 1,3-bis(4-aminophenylsulfone)benzene, 1,4-bis(4-aminophenylsulfone)benzene, 1,3-bis[2-(4-aminophenyl)isopropyl]benzene, 1,4-bis[2-(3-aminophenyl)isopropyl]benzene and 1,4-bis[2-(4-aminophenyl) isopropyl] benzene;

4) diamines with four benzene nuclei, including 3,3'-bis(3-aminophenoxy)biphenyl, 3,3'-bis(4-aminophenoxy)biphenyl, 4,4'-bis(3-aminophenoxy)biphenyl, 4,4'-bis(4-aminophenoxy)biphenyl, bis[3-(3-aminophenoxy)phenyl] ether, bis[3-(4-aminophenoxy)phenyl]ether, bis[4-(3-aminophenoxy)phenyl]ether, bis [4-(4-aminophenoxy) phenyl]ether, bis[3-(3-aminophenoxy)phenyl]ketone, bis[3-(4-aminophenoxy)phenyl]ketone, bis[4-(3-aminophenoxy) phenyl]ketone, bis[4-(4-aminophenoxy)phenyl]ketone, bis [3-(3-aminophenoxy)phenyl] sulfide, bis[3-(4-aminophenoxy)phenyl] sulfide, bis[4-(3-aminophenoxy) phenyl] sulfide, bis[4-(4-aminophenoxy)phenyl] sulfide, bis [3-(3-aminophenoxy)phenyl]sulfone, bis[3-(4-aminophenoxy)phenyl]sulfone, bis[4-(3-aminophenoxy) phenyl]sulfone, bis[4-(4-aminophenoxy)phenyl]sulfone, bis [3-(3-aminophenoxy)phenyl]methane, bis[3-(4-aminophenoxy)phenyl]methane, bis[4-(3-aminophenoxy) phenyl]methane, bis[4-(4-aminophenoxy)phenyl]methane, 2,2-bis[3-(3-aminophenoxy)phenyl]propane, 2,2-bis[3-(4-aminophenoxy)phenyl]propane, 2,2-bis[4-(3-aminophenoxy)phenyl]propane, 2,2-bis[4-(4-aminophenoxy)phenyl] propane, 2,2-bis[3-(3-aminophenoxy)phenyl]-1,1,1,3,3,3-hexafluoropropane, 2,2-bis[3-(4-aminophenoxy)phenyl]-1,1,1,3,3,3-hexafluoropropane, 2,2-bis[4-(3-aminophenoxy) phenyl]-1,1,1,3,3,3-hexafluoropropane and 2,2-bis[4-(4-aminophenoxy)phenyl]-1,1,1 3 3 3-hexafluoropropane.

These may be used alone or in mixtures of two or more. The diamine used may be appropriately selected according to the properties desired.

Preferred among these are aromatic diamine compounds, with 3,3'-diaminodiphenyl ether, 3,4'-diaminodiphenyl ether, 4,4'-diaminodiphenyl ether, paraphenylenediamine, 1,3-bis(3-aminophenyl)benzene, 1,3-bis(4-aminophenyl) benzene, 1,4-bis(3-aminophenyl)benzene, 1,4-bis(4-aminophenyl)benzene, 1,3-bis(4-aminophenoxy)benzene and 1,4-bis(3-aminophenoxy)benzene being preferred for use. Particularly preferred is at least one type of diamine selected from the group consisting of benzenediamines, diaminodiphenyl ethers and bis(aminophenoxy)phenyl.

From the viewpoint of heat resistance and dimensional stability under high temperature, the porous polyimide film to be used for the invention is preferably formed from a polyimide obtained by combination of a tetracarboxylic dianhydride and a diamine, having a glass transition temperature of 240° C. or higher, or without a distinct transition point at 300° C. or higher.

From the viewpoint of heat resistance and dimensional stability under high temperature, the porous polyimide film to be used for the invention is preferably a porous polyimide film comprising one of the following aromatic polyimides.

(i) An aromatic polyimide comprising at least one tetracarboxylic acid unit selected from the group consisting of biphenyltetracarboxylic acid units and pyromellitic acid units, and an aromatic diamine unit, (ii) an aromatic polyimide comprising a tetracarboxylic acid unit and at least one type of aromatic diamine unit selected from the group consisting of benzenediamine units, diaminodiphenyl ether units and bis(aminophenoxy)phenyl units, and/or, (iii) an aromatic polyimide comprising at least one type of tetracarboxylic acid unit selected from the group consisting of biphenyltetracarboxylic acid units and pyromellitic acid units, and at least one type of aromatic diamine unit selected from the group consisting of benzenediamine units, diaminodiphenyl ether units and bis(aminophenoxy)phenyl units.

While not restrictive, the porous polyimide film for use in the invention may be a porous polyimide film with a multilayer structure, having at least two surface layers (A-surface and B-surface), and a macro-void layer sandwiched between the two surface layers. Preferably, the porous polyimide film is a porous polyimide film wherein the macro-void layer has a partition bonded to the surface layers (A-surface and B-surface) and a plurality of macro-voids with mean pore sizes of 10 to 500 µm in the planar direction of the film, surrounded by the partition and the surface layers (A-surface and B-surface), wherein the macro-void layer partition and the surface layers (A-surface and B-surface) each have thicknesses of 0.01 to 20 µm, with a plurality of pores with mean pore sizes of 0.01 to 100 µm, the pores being optionally communicating with each other, and also having a partial or total multilayer structure in communication with the macro-voids, where the total film thickness is 5 to 500 µm and the porosity is 40% or greater and less than 95%.

The total film thickness of the porous polyimide film used for the invention is not limited, but may be 20 to 75 µm according to one mode. Differences in the film thickness may be observed as differences in cell growth rate, cell morphology, cell saturation within the plate, and the like.

According to the invention, when the porous polyimide film used has two different surface layers (A-surface and B-surface), and a macro-void layer sandwiched between the two surface layers, the mean pore size of the holes in the A-surface may differ from the mean pore size of the holes in the B-surface. Preferably, the mean pore size of the holes in the A-surface is smaller than the mean pore size of the holes in the B-surface. More preferably, the mean pore size of the holes in the A-surface is smaller than the mean pore size of the holes in the B-surface, with the mean pore size of the holes in the A-surface being 0.01 to 50 µm, 0.01 µm to 40 µm, 0.01 µm to 30 µm, 0.01 µm to 20 µm or 0.01 µm to 15 µm, and the mean pore size of the holes in the B-surface being 20 µm to 100 µm, 30 µm to 100 µm, 40 µm to 100 µm, 50 µm to 100 µm or 60 µm to 100 µm. Most preferably, the A-surface is a mesh structure having small holes with a mean pore size of no greater than 15 µm, such as 0.01 µm to 15 µm, and the B-surface is a large-hole structure with a mean pore size of 20 µm or greater, such as 20 µm to 100 µm. According to the invention, when the porous polyimide film is used in which the mean pore size of the holes in the A-surface is smaller than the mean pore size of the holes in the B-surface, cells may be seeded on the A-surface, or on the B-surface. Preferably, cells are seeded on the A-surface.

The total film thickness of the porous polyimide film used for the invention can be measured using a contact thickness gauge.

The mean pore size of the surface of the porous polyimide film can be determined by measuring the pore area of 200 or more open holes from a scanning electron micrograph of the porous film surface, and calculating the mean diameter from the average value for the pore areas according to the following formula (1), assuming the pore shapes to be circular.

$$\text{Mean pore size} = 2 \times \sqrt{(Sa/\pi)} \quad (1)$$

(wherein Sa represents the average value for the pore areas)

The porosity of the porous polyimide film used for the invention can be determined by measuring the film thickness and mass of the porous film cut out to a prescribed size, and performing calculation from the basis weight according to the following formula (2).

$$\text{Porosity (\%)} = (1 - w/(S \times d \times D)) \times 100 \quad (2)$$

(wherein S represents the area of the porous film, d represents the total film thickness, w represents the measured mass, and D represents the polyimide density, the polyimide density being defined as $1.34 \text{ g/cm}^3$.)

For example, the porous polyimide films described in International Patent Publication No. WO2010/038873, Japanese Unexamined Patent Publication No. 2011-219585 and Japanese Unexamined Patent Publication No. 2011-219586 may also be used in the invention.

Naturally, the porous polyimide film to which cells are applied in the method of the invention is preferred to be in a state including no biological components other than those of the loaded cells, i.e. in a sterilized state. The method of the invention preferably includes a step of pre-sterilizing the porous polyimide film. A porous polyimide film has very excellent heat resistance and is lightweight, allows free selection of the shape and size, and is easy to treat for sterilization. Any desired sterilization treatment may be conducted, such as dry heat sterilization, steam sterilization, sterilization with a microbicide such as ethanol, or electromagnetic wave sterilization using UV or gamma rays.

The cells that have been seeded on the surface of the porous polyimide film can stably grow and proliferate on the surface and/or in the interior of the film. The cells may be in a variety of different forms, depending on the location of growth and proliferation in the film. According to one mode of the invention, growth may be carried out while moving the surface and interior of the porous polyimide film and changing the form, depending on the type of cell.

4. Application of Cells to Porous Polyimide Film

There are no particular restrictions on the specific steps for application of the cells to the porous polyimide film. It is possible to carry out the steps described throughout the present specification, or to employ any desired method suited for applying cells to a film-like support. Application of cells to the porous polyimide film in the method of the invention includes, but is not limited to, the following modes.

(A) A mode including a step of seeding cells on the surface of a porous polyimide film;

(B) A mode including a step of:

placing a cell suspension on the dried surface of a porous polyimide film, allowing it to stand, or moving the porous polyimide film to promote efflux of the liquid, or stimulating part of the surface to cause absorption of the cell suspension into the film, and retaining the cells in the cell suspension inside the film and allowing the water to flow out; and (C) A mode including a step of:

wetting one or both sides of a porous polyimide film with a cell culture solution or a sterilized liquid, loading a cell suspension into the wetted porous polyimide film, and retaining the cells in the cell suspension inside the film and allowing the water to flow out.

Mode (A) includes a step of directly seeding cells or a cell mass on the surface of a porous polyimide film. Alternatively, it includes a mode of placing a porous polyimide film in a cell suspension and wetting the cell culture solution from the surface of the film.

Cells seeded on the surface of a porous polyimide film adhere to the porous polyimide film and infiltrate into the interiors of the pores. Preferably, the cells adhere spontaneously to the porous polyimide film without applying any particular exterior physical or chemical force. The cells that have been seeded on the surface of the porous polyimide film can stably grow and proliferate on the surface and/or in the interior of the film. The cells may be in a variety of different forms, depending on the location of the film used for growth and proliferation.

For mode (B), a cell suspension is placed on the dried surface of a porous polyimide film. The porous polyimide film is allowed to stand, or the porous polyimide film is moved to promote efflux of the liquid, or part of the surface is stimulated to cause absorption of the cell suspension into the film, so that the cell suspension permeates into the film. While it is not our intention to be constrained by theory, this is believed to be due to the properties of each of the surface forms of the porous polyimide film. According to this mode, the cells are absorbed and seeded in the locations of the film where the cell suspension has been loaded.

Alternatively, as according to mode (C), after all or a portion of one or both sides of the porous polyimide film has been wetted with the cell culture solution or sterilized liquid, the cell suspension may be loaded into the wetted porous polyimide film. This will significantly increase the transit rate of the cell suspension.

For example, a method of wetting a portion of the film edges, for the main purpose of preventing fly loss of the film, may be used (hereunder referred to as "single-point wetting method"). The single-point wetting method is nearly the same as the dry method (mode (B)) in which the film essentially is not wetted. However, it is possible that cell solution permeation through the film is more rapid at the small wetted portions. There may also be used a method in which all of one or both sides of the porous polyimide film that have been thoroughly wetted (hereunder this will also be referred to as "wet film") is loaded with a cell suspension (this will hereunder be referred to as "wet film method"). In this case, the entire porous polyimide film has a greatly increased transit rate for the cell suspension.

According to modes (B) and (C), the cells in the cell suspension are retained in the film, while the water flows out. This allows treatment such as increasing the concentration of cells in the cell suspension and flowing out of unwanted non-cellular components together with the water.

Mode (A) will also be referred to as "natural seeding", and modes (B) and (C) as "suction seeding".

Preferably, but not restrictively, the viable cells are selectively retained in the porous polyimide film. Thus, according to a preferred mode of the invention, the viable cells are retained in the porous polyimide film, and the dead cells preferentially flow out together with the water.

The sterilized liquid used for mode (C) is not particularly restricted, and may be a sterilized buffering solution or sterilized water. A buffering solution may be, for example, (+) or (−) Dulbecco's PBS, or (+) or (−) Hank's Balanced Salt Solution. Examples of buffering solutions are listed in Table 1 below.

TABLE 1

| Component | Concentration (mmol/L) | Concentration (g/L) |
| --- | --- | --- |
| NaCl | 137 | 8.00 |
| KCl | 2.7 | 0.20 |
| $Na_2HPO_4$ | 10 | 1.44 |
| $KH_2PO_4$ | 1.76 | 0.24 |
| pH (−) | 7.4 | 7.4 |

In the method of the invention, application of cells to the porous polyimide film further includes a mode of adding adherent cells in a floating state as a suspension together with the porous polyimide film, to adhere the cells with the film (entangling). For example, for application of the cells to the porous polyimide film in the method of the invention, the cell culture medium, the cells and one or more of the porous polyimide films may be placed in the cell culturing vessel. When the cell culture medium is a liquid, the porous polyimide film is in a floating state in the cell culture medium. The cells can adhere to the porous polyimide film due to the properties of the porous polyimide film. Thus, even with cells that are not suited for natural suspension culture, the porous polyimide film allows culturing in a floating state in the cell culture medium. The cells preferably spontaneously adhere to the porous polyimide film. Here, "adhere spontaneously" means that the cells are retained on the surface or in the interior of the porous polyimide film without applying any particular exterior physical or chemical force.

5. Cell Culturing

The invention includes culturing of cells that have been applied to a porous polyimide film and production of a substance by the cells.

Application of cells to a porous polyimide film and their culturing is described as follows in PCT/JP2014/070407.

Cell culturing can be classified into culturing where the cultured cells are adhesion culture-type cells or suspension culture-type cells, depending on the state in the cell culture. Adhesion culture-type cells are cultured cells that adhere and grow on a culturing vessel, with the medium being exchanged at the time of subculture. Suspension culture-type cells are cultured cells that grow in a suspended state in a medium, and generally the medium is not exchanged with each subculture but dilution culture is carried out. Because suspension culture allows culturing in a suspended state, i.e. in a liquid, mass culturing becomes possible, and because it is three-dimensional culturing, unlike with adherent cells that grow only on the culturing vessel surface, the advantage of increased culturable cell count per unit space is afforded.

In the method of the invention, when the porous polyimide film is used in a state suspended in the cell culture medium, two or more fragments of the porous polyimide film may be used. Since the porous polyimide film is a flexible thin-film, using such fragments that are suspended in the culture solution, for example, allows a porous polyimide film with a large surface area to be added into a fixed volume of cell culture medium. In the case of normal culturing, the container base area constitutes the area limit in which cell culture can be accomplished, but with cell culturing using the porous polyimide film of the invention, all of the large surface area of the previously added porous polyimide film constitutes area in which cell culturing can be accomplished. The porous polyimide film allows the cell culture solution to pass through, allowing supply of nutrients, oxygen and the like even into the folded film, for example.

The sizes and shapes of the porous polyimide film fragments are not particularly restricted. The shapes may be as desired, such as circular, elliptical, quadrilateral, triangular, polygonal or string-like.

Because the porous polyimide film of the invention is flexible, it can be used with varying shapes. Instead of a flat form, the porous polyimide film can also be used by working into a three-dimensional shape. For example, porous polyimide films may be: i) folded, ii) wound into a roll, iii) connected as sheets or fragments by a filamentous structure, or iv) bound into a rope, for suspension or fixing in the cell culture medium in the cell culturing vessel. By forming into shapes such as i) to iv), it is possible to place a large amount of porous polyimide films into a fixed volume of cell culture medium, similar to using fragments. Furthermore, since each fragment can be treated as an aggregate, it is possible to aggregate and move the cell masses together, for overall high applicability.

With the same concept as fragment aggregates, two or more porous polyimide films may be used in a layered form either above and below or left and right in the cell culture medium. Layering includes a mode in which portions of the porous polyimide films overlap. Layered culturing allows culturing of cells at high density in a narrow space. It is also possible to further layer a film on a film on which cells are already growing, setting it to create a multilayer of different cell types. The number of layered porous polyimide films is not particularly restricted.

Two or even more forms of the cell culturing method described above may be used in combination. For example, using any of the methods of modes (A) to (C), first the cells may be applied to the porous polyimide film and then the cell-adhered porous polyimide film may be used for suspension culture. Alternatively, the step of application to the porous polyimide film may be a combination of two or more of the methods of any of modes (A) to (C).

In the method of the invention, preferably the cells grow and proliferate on the surface or in the interior of the porous polyimide film. By the method of the invention, it is possible to carry out continuous growth of cells for 2 days or longer, more preferably 4 days or longer and even more preferably 6 days or longer.

In the method of the invention, application of cells and culturing are carried out on a porous polyimide film, thereby allowing culturing of large volumes of cells to be accomplished since large numbers of cells grow on the multisided connected pore sections on the inside, and the surfaces on the porous polyimide film.

Moreover, in the method of the invention, it is possible to culture large volumes of cells efficiently while drastically reducing the amount of medium used for cell culturing compared to the prior art. For example, large volumes of cells can be cultured even when all or a portion of the porous polyimide film is not in contact with the liquid phase of the cell culture medium. Also, the total volume of the cell culture medium in the cell culturing vessel, with respect to the total porous polyimide film volume including the cell survival zone, can be significantly reduced below that of methods of the prior art.

Using the method of the invention, cells can be satisfactorily cultured for a long time even under conditions in which the total volume of the cell culture medium in the cell culturing vessel is 10,000 times or less of the total sum of the porous polyimide film volume including the cell survival zone. Moreover, cells can be satisfactorily cultured for a long time even under conditions in which the total volume of the cell culture medium in the cell culturing vessel is 1000 times or less of the total sum of the porous polyimide film volume including the cell survival zone. In addition, cells can be satisfactorily cultured for a long time even under conditions in which the total volume of the cell culture medium in the cell culturing vessel is 100 times or less of the total sum of the porous polyimide film volume including the cell survival zone. Cells can also be satisfactorily cultured for a long time even under conditions in which the total volume of the cell culture medium in the cell culturing vessel is 10 times or less of the total sum of the porous polyimide film volume including the cell survival zone.

Conventionally known three-dimensional culturing base materials for cells include the porous polystyrene base material Alvetex®(ReproCell), the polycaprolactone base material 3D Insert-PCL (3D Biotech), and the polystyrene base material 3D Insert-PS (3D Biotech). When cells have been cultured using a porous polyimide film according to the method of the invention, the substance productivity per unit volume is much higher compared to when cells have been cultured using a conventionally known three-dimensional culture base material.

Moreover, in the method of the invention, the cells are cultured in the porous polyimide film without forming cell masses (spheroids). Since the cells under such culturing conditions can stably grow for prolonged periods without detaching, it is possible to obtain the produced substance as a clarified liquid.

In addition, the porous polyimide film can be frozen and stored while supporting large volumes of cells. The porous polyimide film can also be thawed when desired, and used for production of protein, without passing through a preculturing step. The ability of the cells to produce the substance does not decrease even after the freezing and thawing steps. For use of thawed cells in the prior art, it has been necessary to preculture the thawed cells and then culture the surviving cells after supporting them on a desired base material or support. By using the porous polyimide film, however, it is possible to carry out culturing, freezing, storage, thawing and re-culturing of cells while they are adhering to the porous polyimide film, without a preculturing step after thawing as has been required in the prior art. Therefore, by preparing large amounts of a frozen cell-supporting porous polyimide films, large volumes of cells can be used at any desired time without an amplifying culturing step. Such steps of freezing, storage, thawing and culturing may be repeated several times.

6. Cell Culturing and Substance Production System and Culturing Conditions

In the method of the invention, the cell culturing and substance production system and culturing conditions may be set as appropriate according to the type of cells used. Culturing methods suited for various cells including animal cells, plant cells and bacteria are publicly known, and a person skilled in the art may carry out culturing of cells suited for the porous polyimide film, using any publicly known method. The cell culture medium may also be prepared as appropriate for the type of cells.

Cell culture methods and cell culture media for animal cells may be found in the Cell Culture Media Catalog of Lonza Group, Ltd., for example. Cell culture methods and cell culture media for plant cells may also be found in the Plant Tissue Culturing Media Series by Wako Corp. Japan, for example. Cell culture methods and cell culture media for bacteria may also be found in the General Bacterial Media Catalog of BD Corp., for example. The cell culture medium to be used in the method of the invention may be in any form such as a liquid medium, semi-solid medium or solid medium. Also, a liquid medium in mist form may be sprayed into the cell culturing vessel to contact the medium with the cell-supporting porous polyimide film.

The cell culture using a porous polyimide film may also be combined with another suspension culture support such as a microcarrier, cellulose sponge or the like.

The method of the invention is not particularly restricted in terms of the form and scale of the system used for the culturing, and any scale from cell culturing dish to a flask, plastic bag, test tube or large tank may be used, as appropriate. These include, for example, Cell Culture Dish by BD Falcon, and Nunc Cell Factory by Thermo Scientific. By using a porous polyimide film according to the invention, it has become possible to carry out culturing even of cells that have not been capable of natural suspension culture, using an apparatus intended for suspension culture, in a state similar to suspension culturing. The apparatus for suspension culture that is used may be, for example, a spinner flask or rotating culturing flask by Corning, Inc. As an environment allowing a similar function to be obtained, there may be used a hollow fiber culturing system such as the FiberCell® System by Veritas.

According to the invention, the cells may also be cultured under stationary culture conditions. By intermittently replacing the medium, it is possible to isolate the useful substance that is produced. Application of the porous polyimide film can also drastically increase efficiency in stationary culturing using a single use culturing bag.

According to the invention, the cells may also be cultured under rotating culture or stirred conditions. Continuously swinging the single use culturing bag will allow its use on a very large scale. The same also applies for rotating culture or stirred culture with a spinner flask. Moreover, in each of these methods, a continuous or intermittent medium exchange system may be mounted to tailor it for long term culturing.

According to the invention, the cells can be cultured in a continuous manner. For example, the culturing in the method of the invention may be carried out in a manner with continuous circulation such as continuous addition and recovery of the medium on the porous polyimide film, or exposure of the porous polyimide film sheet to air using an open apparatus.

Cell culturing according to the invention may be carried out in a system in which a cell culture medium is continuously or intermittently supplied to a cell culturing vessel from cell culture medium supply means installed outside of the cell culturing vessel. The system may be such that the cell culture medium is circulated between the cell culture medium supply means and the cell culturing vessel.

The invention includes a mode in which a cell culturing apparatus is set in an incubator and the cells are cultured. When it is to be used in a system in which the cell culture medium is continuously or intermittently supplied to the cell culturing vessel from cell culture medium supply means installed outside of the cell culturing vessel, the system may be a cell culturing apparatus including a culturing unit which is the cell culturing vessel, and a culture medium-supply unit which is the cell culture medium supply means, wherein the culturing unit is a culturing unit that houses one or more porous polyimide films to support cells, and that comprises a culture medium supply port and a culture medium discharge port, and the culture medium-supply unit is a culture medium-supply unit comprising a culture medium housing vessel, a culture medium supply line, and a liquid conveyance pump that conveys the medium through the culture medium supply line, the first end of the culture medium supply line contacting the medium in the culture medium housing vessel, and the second end of the culture medium supply line being in communication with the culturing unit interior via the culture medium supply port of the culturing unit.

In the cell culturing apparatus, the culturing unit may be a culturing unit that does not comprise an air supply port and an air discharge port, or it may be a culturing unit that comprises an air supply port and an air discharge port. Even if the culturing unit does not comprise an air supply port and air discharge port, the oxygen, etc. necessary for cell culturing is adequately supplied to the cells through the medium. Furthermore, in the cell culturing apparatus described above, the culturing unit may further comprise a culture medium discharge line, the first end of the culture medium discharge line being connected to the culture medium housing vessel, the second end of the culture medium discharge line being in communication with the culturing unit interior via the culture medium discharge port of the culturing unit, and the medium being able to circulate through the culture medium-supply unit and the culturing unit.

7. Production of Substance by Cells

The invention produces a desired substance by cells, by culturing the cells as described above. The produced substance may be a substance accumulating inside the cells, or a substance secreted from the cells. The produced substance may be collected by a known method, according to the type and properties of the substance. When the substance is secreted from the cells, the substance can be recovered from the cell culture medium. When the produced substance is a substance that accumulates inside the cells, the cells may be disrupted by a known method such as chemical treatment using a cytolytic agent or the like, ultrasonic treatment or physical treatment using a homogenizer or a shredding DispoTube, to move the substance out of the cells and recover it. The method of disrupting the cells may be any one applied as appropriate by a person skilled in the art depending on the type of cells and the type of substance.

II. Substance-producing Apparatus

The invention also relates to an apparatus for production of a substance by cell culturing, to be used in the method of the invention, the apparatus including a porous polyimide film. In the substance-producing apparatus of the invention, the porous polyimide film may be used in a fixed state, or it may be used in a floating state in the cell culture medium, and it may be either placed in the medium or exposed from the medium. In the substance-producing apparatus, two or more porous polyimide films may be layered either above and below or left and right. The layered aggregates or cluster may be either placed in the medium or exposed from the medium.

The substance-producing apparatus for cell culturing of the invention may be a known cell culturing apparatus, in any desired form so long as it includes a porous polyimide film. The shape and scale of the culturing apparatus is not particularly restricted, and any scale from a dish or test tube to a large tank may be used, as appropriate. These include, for example, Cell Culture Dish by BD Falcon, and Nunc Cell Factory by Thermo Scientific. By using a porous polyimide film according to the invention, it has become possible to carry out culturing even of cells that have not been suitable for natural suspension culture, by using an apparatus intended for suspension culture, in a state similar to suspension culture. The apparatus for suspension culture that is used may be, for example, a spinner flask or rotating culture flask by Corning, Inc. As an environment allowing a similar function to be obtained, there may be used a hollow fiber culturing system such as the FiberCell® System by Veritas.

The substance-producing apparatus for cultured cells according to the invention may be a continuous circulating or open apparatus, wherein medium is continuously added to and recovered from sheets on the mesh, and the method may also be carried out with a type that exposes the porous polyimide film sheets to air.

Means may also be provided for recovering the substance that has been produced by the cells according to the invention. For example, by directly connecting a semipermeable membrane or the like to circulating added medium, it is possible to construct an efficient and prolonged culturing/removal system in which sugars or amino acids are added while removing unwanted substances such as lactic acid.

III. Kit

The present invention also relates to a kit for use in the method of the invention, the kit including a porous polyimide film.

The kit of the invention may include constituent elements necessary for cell culturing and substance production and recovery, in addition to the porous polyimide film, as appropriate. For example, it may include the cells to be applied to the porous polyimide film, the cell culture medium, a continuous medium-supply apparatus, a continuous medium circulating apparatus, a scaffold or module to support the porous polyimide film, a cell culturing apparatus, ELISA to confirm the substance production, cell disruption means (for example, a cytolytic agent and a shredding Dispo Homogenizer), substance recovering means (for example, an ultrafiltration centrifugation tube, coprecipitation reagent set and tube, and reagents such as antibodies), and the instruction manual for the kit.

While not restrictive, one mode includes a package containing either one or a plurality of sterilized porous polyimide films stored in a transparent pouch, in a form allowing their use for cell culturing, or a kit having a sterile liquid encapsulated together with a porous polyimide film in the same pouch, in the form of an integrated film/liquid allowing efficient suction seeding.

IV. Use

The invention further includes use of a porous polyimide film for the method of the invention described above.

EXAMPLES

The present invention will now be explained in greater detail by examples. It is to be understood, however, that the invention is not limited to these examples. A person skilled in the art may easily implement modifications and changes to the invention based on the description in the present specification, and these are also encompassed within the technical scope of the invention. Unless otherwise specified, the term "porous polyimide film" refers to a porous polyimide film with a total film thickness of 25 µm and a porosity of 73%. Each porous polyimide film had at least two different surface layers (A-surface and B-surface), and a macro-void layer sandwiched between the two surface layers. The mean pore size of the holes in the A-surface was 6 µm, and the mean pore size of the holes in the B-surface was 46 µm.

The porous polyimide films used in the following examples were prepared by forming a polyamic acid solution composition including a polyamic acid solution obtained from 3,3',4,4'-biphenyltetracarboxylic dianhydride (s-BPDA) as a tetracarboxylic acid component and 4,4'-diaminodiphenyl ether (ODA) as a diamine component, and polyacrylamide as a coloring precursor, and performing heat treatment at 250° C. or higher.

<Cells and Materials Used>

Normal human skin fibroblasts (Lonza, product code CC-2511)

Normal human fibroblast-like synovial membrane cells HFLS (Cell Applications, Inc.)

Chronic rheumatoid arthritis patient-derived fibroblast-like synovial membrane cells HFLS-RA (Cell Applications, Inc.)

HepG2 (HEPG2-500 by CET (Cellular Engineering Technologies, Inc.))

CHO-K1 (cat. 85051005 by Public Health England)

CHO DP-12 (ATCC CRL-12445)

CHO-K1 medium (Ham's F-12 087-08335 by Wako Pure Chemical Industries, Ltd.)

CHO DP-12 medium (IMDM 098-06465 by Wako Pure Chemical Industries, Ltd.)

Cell Counting Kit 8 (CK04, Dojindo Laboratories)

Stainless steel mesh (60 mesh E9117 by Qholia)

2 cm×2 cm sterilized square vessel (cat. 103 by Thermo Fisher Scientific)

Penicillin-Streptomycin-Amphotericin B Suspension (X100) (161-23181 by Wako Pure Chemical Industries, Ltd.)

Microscope, image software LSM 700 by Carl Zeiss, software: ZEN

Example 1

Spontaneous Substance Production by Normal Human Skin Fibroblasts

For this example, normal human skin fibroblasts were used for seeding and cell culturing on a porous polyimide film, and the amount of fibronectin produced on the petri dish was confirmed.

After adding 1 ml of cell culture medium (2% FBS, Fibroblast Media, Lonza) to a 2 cm×2 cm square sterilized vessel, a 1.4 cm-square porous polyimide film was immersed in the medium with the A-surface of the mesh structure facing upward. Separately, there was prepared a normal human skin fibroblast suspension with normal human skin fibroblasts suspended at $4.2\times10^6$ cells per 1 ml of medium (of which viable cells were $4.2\times10^6$ and dead cells were $4.0\times10^4$, for a viable cell rate of 99%). The cell suspension was added to the cell culture medium in the square vessel at $4\times10^4/cm^2$ per sheet, and culturing was carried out for 14 days in the square vessel. There was also prepared a normal human skin fibroblast suspension with normal human skin fibroblasts suspended at $3.0\times10^6$ cells per 1 ml of medium (of which viable cells were $2.9\times10^6$ and dead cells were $1.6\times10^5$, for a viable cell rate of 95%). After adding 1 ml of cell culture medium to a 5 $cm^2$ petri dish, adding the cell suspension at $1.0\times10^4/cm^2$ and culturing for 43 days, cell culturing was carried out in a petri dish.

There were prepared a 5 cm² petri dish containing a single cell-cultured sheet and a 5 cm² petri dish in which cells had been cultured without the sheet.

The medium supernatant was discarded, 1 ml of fresh cell culture medium was added to each, incubation was carried out for 2 days at 37° C. with 5% $CO_2$, and the medium supernatant was recovered. The amount of fibronectin in the recovered supernatant was quantified by ELISA (Table 2). Table 2 shows the amounts of fibronectin spontaneously produced using human skin fibroblasts, using the porous polyimide film sheet and petri dish as different culturing scaffolds. As shown in Table 2, using the porous polyimide film sheet resulted in more than twice the amount of spontaneous production of fibronectin than when using the petri dish.

TABLE 2

Comparison of fibronectin production per unit area (Example 1)

| Culturing scaffold | Fibronectin (ng/cm²) |
|---|---|
| Porous polyimide film | $3.2 \times 10^3$ |
| Petri dish | $1.4 \times 10^3$ |

Example 2

Spontaneous Substance Production by Normal Human Fibroblast-like Synovial Membrane Cells HFLS and Chronic Rheumatoid Arthritis Patient-Derived Fibroblast-like Synovial Membrane Cells HFLS-RA For this example, normal human fibroblast-like synovial membrane cells HFLS and chronic rheumatoid arthritis patient-derived fibroblast-like synovial membrane cells HFLS-RA were used for seeding and cell culturing on porous polyimide films, after which the amounts of IL-6 production in the petri dishes were confirmed.

After adding 1 ml of cell culture medium (10% FBS, Synoviocyte Growth Medium, Cell Applications, Inc.) to a 2 cm×2 cm square sterilized vessel, a 1.4 cm-square porous polyimide film was immersed in the medium with the A-surface of the mesh structure facing upward. Separately, an HFLS cell suspension was prepared with the HFLS cells suspended at $1.5 \times 10^6$ cells per 1 ml of medium (of which $1.4 \times 10^6$ were viable cells and $2.0 \times 10^4$ were dead cells, for a viable cell rate of 99%). The cell suspension was added to the cell culture medium in the square vessel at $4.0 \times 10^4/cm^2$ per sheet, and culturing was carried out for 13 days in the square vessel. Also, 1 ml of cell culture medium was added to a 5 cm² petri dish, and an HFLS cell suspension was separately prepared with the HFLS cells suspended at $5.9 \times 10^5$ cells per 1 ml of medium (of which $5.7 \times 10^5$ were viable cells and $2.0 \times 10^4$ were dead cells, for a viable cell rate of 97%). The cell suspension was added at $7 \times 10^3/cm^2$ and cultured for 8 days, and cell culturing was carried out in a petri dish.

Similarly, an HFLS-RA cell suspension was prepared with the HFLS-RA cells suspended at $2.2 \times 10^6$ cells per 1 ml of medium, of which $2.0 \times 10^6$ were viable cells and $1.6 \times 10^5$ were dead cells, for a viable cell rate of 93%. The cell suspension was added to the cell culture medium in the square vessel at $4.0 \times 10^4/cm^2$ per sheet, and culturing was carried out for 13 days in the square vessel. Also, 1 ml of cell culture medium was added to a 5 cm² petri dish, and an HFLS-RA cell suspension was separately prepared with the HFLS-RA cells suspended at $5.8 \times 10^5$ cells per 1 ml of medium (of which $5.6 \times 10^5$ were viable cells and $2.0 \times 10^4$ were dead cells, for a viable cell rate of 97%). The cell suspension was added at $7.0 \times 10^3/cm^2$ and cultured for 8 days, and cell culturing was carried out in a petri dish.

Two 5 cm² petri dishes were prepared, and one cell cultured HFLS sheet and one HFLS-RA sheet was placed in them, respectively. Also prepared were 5 cm² petri dishes of cell cultured HFLS and HFLS-RA without the sheets.

The medium supernatant was discarded, 1 ml of fresh cell culture medium was added to each, incubation was carried out for 3 days at 37° C. 5% $CO_2$, and the medium supernatant was recovered. The amount of IL-6 in the recovered supernatant was quantified by ELISA (Table 3). Table 3 shows the amounts of IL-6 spontaneously produced using the normal human fibroblast-like synovial membrane cells, with the porous polyimide film sheets and petri dishes used as different culturing scaffolds. As shown in Table 3, using the porous polyimide film sheets resulted in more than about 25 times the amount of spontaneous production of IL-6 with normal human fibroblast-like synovial membrane cells HFLS and more than about 5 times the amount with chronic rheumatoid arthritis patient-derived fibroblast-like synovial membrane cells HFLS-RA, than when using the petri dishes.

TABLE 3

IL-6 production by human fibroblast-like synovial membrane cells (Example 2)

| Cells and culturing scaffold | IL-6 (pg/ml) |
|---|---|
| Human fibroblast-like synovial membrane cells/Porous polyimide film | $2.7 \times 10^2$ |
| RA human fibroblast-like synovial membrane cells/Porous polyimide film | $3.5 \times 10^3$ |
| Human fibroblast-like synovial membrane cells/Petri dish | $1.1 \times 10^1$ |
| RA human fibroblast-like synovial membrane cells/Petri dish | $7.1 \times 10^2$ |

Example 3

Spontaneous Albumin Production by Human Hepatic Cancer-derived Cell Line, HepG2 Cells For this example, the human hepatic cancer-derived cell line HepG2 was used for seeding and cell culturing on a porous polyimide film, after which the amount of albumin production spontaneously released into the medium during a fixed period was confirmed.

After adding 1 ml of cell culture medium (10% FBS, HEPG2.E.MEDIA-450, Cellular Engineering Technologies Inc.) into a 2 cm×2 cm square sterilized vessel, a 1.4 cm-square porous polyimide film was immersed in the medium with the A-surface of the mesh structure facing upward. Separately, a HepG2 cell suspension was prepared with the HepG2 cells suspended at $1.6 \times 10^6$ cells per 1 ml of medium (of which $1.4 \times 10^6$ were viable cells and $1.3 \times 10^5$ were dead cells, for a viable cell rate of 92%). The cell suspension was added to the cell culture medium in the square vessel at $2 \times 10^4/cm^2$ per sheet, and culturing was carried out for 21 days in the square vessel. Also, 2 ml of cell culture medium was added to a 10 cm² petri dish and the cell suspension was added at $2 \times 10^4/cm^2$ for cell culturing for 21 days, and cell culturing was carried out in a petri dish.

There were prepared a 10 cm² petri dish containing three cell-cultured sheets or a single sheet, and a 10 cm² petri dish in which cells had been cultured. The medium supernatant was discarded, 2 ml of fresh cell culture medium was added to each, incubation was carried out for 3 hours at 37° C. with 5% $CO_2$, and the medium supernatant was recovered. The amount of albumin in the recovered supernatant was quantified by ELISA (Tables 4 and 5). Tables 4 and 5 show the amounts of albumin spontaneously produced using the HepG2 cells, with the porous polyimide film sheets and petri dish used as different culturing scaffolds. Table 4 shows the amount of albumin production per unit area of the film, and Table 5 shows the amount of albumin production per cell. Since there was no correlation between the number of sheets present and the albumin production amount per cell, the production amount per porous polyimide film being constant, it is therefore expected that substance production proceeds in a proportional manner with increasing cell count.

TABLE 4

Albumin production per unit area by HepG2 cells (Example 3)

| Culturing scaffold and cell amount | Albumin (ng/cm²) |
|---|---|
| Porous polyimide films: 3 sheets | $2.8 \times 10^2$ |
| Porous polyimide films: 1 sheet | $3.2 \times 10^2$ |
| Petri dish | $2.5 \times 10^1$ |

TABLE 5

Albumin production per cell by HepG2 cells (Example 3)

| Culturing scaffold and cell amount | Albumin (pg/cell) |
|---|---|
| Porous polyimide films: 3 sheets | $2.8 \times 10^{-1}$ |
| Porous polyimide films: 1 sheet | $2.7 \times 10^{-1}$ |
| Petri dish | $9.7 \times 10^{-2}$ |

Example 4

Substance Production by G-CSF-producing CHO-K1 Cell Line

For this example, G-CSF was produced by cell culturing using G-CSF-producing CHO-K1 cells, and the amount of G-CSF released into the medium was measured.

A suspension was prepared with the G-CSF-producing CHO-K1 cells suspended at $4.1 \times 10^6$ cells per 1 ml of medium (of which $3.6 \times 10^6$ were viable cells and $4.1 \times 10^5$ were dead cells, for a viable cell rate of 90%). The cell suspension was seeded on the A-surface of a 8 ×12.5 cm rectangular porous polyimide film at $4.1 \times 10^4/cm^2$ per sheet, and 20 ml of cell culture medium (1% FBS, Ham's F-12, product of Wako Pure Chemical Industries, Ltd.) was added to a 10×14 cm rectangular sterilized vessel, which was then immersed twice into medium. The medium was exchanged twice a week in the rectangular vessel, and culturing was carried out for 7 days. The medium supernatant of the cultured sheet was removed, 20 ml of fresh cell culture medium was added, incubation was performed for 24 hours at 37° C. with 5% $CO_2$, and the medium supernatant was recovered. The amount of G-CSF in the recovered supernatant was quantified by ELISA (Table 6).

TABLE 6

| Culturing scaffold | G-CSF (pg/cell/day) |
|---|---|
| Porous polyimide film | $3.4 \times 10^{-2}$ |

Example 5

Substance Production by Anti-human IL-8-producing CHO DP-12 Cells

For this example, the amount of anti-human IL-8 antibody produced and released in the medium by cell culturing using human anti-IL-8 antibody-producing CHO DP-12 cells was measured, to determine the efficiency of a cell culture system using a porous polyimide film. As a comparative example, the amount of antibody production obtained by culturing in a common petri dish was also examined.

After adding 0.5 ml of cell culture medium (2% FBS, IMDM, product of Wako Pure Chemical Industries, Ltd.) to a 2 cm×2 cm square sterilized vessel, each sterilized 1.4 cm-square porous polyimide film was immersed therein with the A-surface of the mesh structure facing upward. A human anti-IL-8-producing CHO DP-12 cell suspension was added to the sheets in each medium at $4 \times 10^4$ cells per sheet, and continuous cell culturing was carried out, with medium exchange at a frequency of twice a week. After cell culturing for 85 days, a CCK8 was used to measure the cell count. Two cell-cultured sheets were each placed in a 10 cm² petri dish, 2 ml of cell culture medium was added to each, and incubation was performed for 24 hours at 37° C. with 5% $CO_2$, after which the medium supernatants were recovered. The amount of anti-human IL-8 antibody in the recovered supernatant was quantified by ELISA (Porous polyimide film 1 and Porous polyimide film 2 in Table 7).

After adding 12 ml of cell culture medium to a 60 cm² petri dish, there was prepared a suspension of $5.3 \times 10^6$ human anti-IL-8-producing CHO DP-12 cells per 1 ml of medium (of which $5.3 \times 10^6$ were viable cells and 2.8×105 were dead cells, for a viable cell rate of 95%), seeding the cells at $2.0 \times 10^4/cm^2$. After 24 hours of culturing, the medium supernatant was recovered. The amount of human anti-IL-8 antibody in the recovered supernatant was quantified by ELISA (Petri dish 1 and Petri dish 2 in Table 7).

TABLE 7

| Culturing scaffold | Human anti-IL-8 antibody (pg/cell/day) |
|---|---|
| Porous polyimide film 1 | 16.2 |
| Porous polyimide film 2 | 19.3 |
| Petri dish 1 | 5.4 |
| Petri dish 2 | 4.6 |

Surprisingly, when the porous polyimide films were used as culturing scaffolds, the amount of substance production in each cell of the CHO-K1 cells increased by more than three times compared to using the petri dishes.

Example 6

Substance Production by Anti-human IL-8-producing CHO DP-12 Cells

For this example, in cell culturing using human anti-IL-8 antibody-producing CHO DP-12 cells, where the cultured cells were frozen while on the porous polyimide film sheet, rethawed and then cultured, it was examined whether or not this produced any change in anti-human IL-8 antibody produced and released into the medium when ordinary culturing was continued.

After adding 0.5 ml of cell culture medium (2% FBS, IMDM, product of Wako Pure Chemical Industries, Ltd.) to a 2 cm×2 cm square sterilized vessel, six sterilized 1.4 cm-square porous polyimide films were immersed therein with the A-surfaces of the mesh structures facing upward. A human anti-IL-8-producing CHO DP-12 cell suspension was added to the sheets in each medium at $4 \times 10^4$ cells per sheet, and continuous cell culturing was carried out, with medium exchange at a frequency of twice a week. After cell culturing for 78 days, a CCK8 was used to measure the cell count. Next, two of the six porous polyimide film sheets supporting cells by cell culturing were each placed in a 10 $cm^2$ petri dish, 2 ml of cell culture medium was added to each, and incubation was performed for 24 hours at 37° C. with 5% $CO_2$, after which the medium supernatants were recovered. The amounts of anti-human IL-8 antibody in the recovered supernatants were quantified by ELISA (Non-frozen sheet 1 and Non-frozen sheet 2 in Table 8).

Also, four of the six porous polyimide film sheets supporting cells by cell culturing were transferred to cryopreservation bags under sterile conditions, and 3 ml of CELL-BANKER was added as a cell cryopreservation liquid. After freezing with a programmed freezer at −80° C. under two different conditions (1° C. per minute or 1° C. every 10 minutes), it was stored at −80° C. for 24 hours and transferred into liquid nitrogen. After 3 days, the contents were thawed by heating the bag at 37° C., 2 ml of medium was added and the mixture was allowed to stand in an incubator for 24 hours, after which each sheet was transferred to a 2 cm×2 cm square sterilized vessel, 1 ml of cell culture medium was added and culturing was continued for 3 days. Next, the sheets were each placed in a 10 $cm^2$ petri dish, 2 ml of cell culture medium was added to each, and incubation was performed for 24 hours at 37° C. with 5% $CO_2$, after which the medium supernatants were recovered. The amounts of anti-human IL-8 antibody in the recovered supernatants were quantified by ELISA (Frozen sheets 1 to 4 in Table 8). No change in anti-IL-8 production was seen due to the freezing.

TABLE 8

|  | Human anti-IL-8 antibody (pg/cell/day) |
| --- | --- |
| Frozen sheet 1 | 26.4 |
| Frozen sheet 2 | 18.0 |
| Frozen sheet 3 | 24.0 |
| Frozen sheet 4 | 28.7 |
| Non-frozen sheet 1 | 16.2 |
| Non-frozen sheet 2 | 19.3 |

Example 7

Confirming Growth by Gas Phase Subculturing During Long Term Culturing of Human Skin Fibroblasts After adding 2 ml of medium to a 6 cm-diameter petri dish, human skin fibroblasts were seeded on the A-surfaces of the mesh structures of 1.4 cm-square sterilized porous polyimide films, at $4 \times 10^4$ cells per sheet, and culturing was carried out for 1 month. The sheets were then cut into quarter portions and culturing was continued for a total of 230 days of culturing. Next, three 1.4 cm-square stainless steel meshes were stacked and set at the center of a 3.5 cm dish, and the porous polyimide film was placed thereover and sandwiched with two empty 1.4 cm-square sterilized porous polyimide films. When 1 ml of medium was added in this state, the medium reached approximately the height of the sheets. They were then directly transferred into a $CO_2$ incubator, the medium was exchanged at a rate of twice per week, and cell culturing was subsequently continued.

After 7 days of culturing, each sheet was separately isolated and culturing was continued in each sheet. After 7, 10, 16, 21, 28, 42 and 56 days, the cell counts were measured using a CCK8, and the cell growth behaviors on the original sheets and the subsequently set empty porous polyimide films were observed with a CCK8, based on staining. The behavior was observed whereby the cells efficiently migrated from the porous polyimide films in which long term culturing of human skin fibroblasts had taken place, to the empty porous polyimide films, and continuously proliferated. The results are shown in FIG. 1.

ELISA measurement was performed, using a human skin fibroblast-cultured sheet wherein continuous long term culturing had been carried out for 294 days on a porous polyimide film without gas phase subculturing, and a base sheet that had been gas-phase subcultured for the same period up to the 230th day and two sheets (upper and lower) that had been cultured by gas phase culturing for 56 days after subculturing, and the fibronectin produced by the living human skin fibroblasts was compared with the amount of fibronectin released in 24 hours into the medium in which the sheets had been cultured. Stable production of fibronectin was confirmed without any effect of the culturing period or gas phase subculturing. The results are shown in Table 9. For comparison, the fibronectin amount produced from two sheets cultured for 13 days with a porous polyimide film was also recorded.

TABLE 9

| Entry (days cultured and condition) | Fibronectin production per area (ng/$cm^2$/day) |
| --- | --- |
| Porous polyimide film, normal culturing, day 13 (Run 1) | 480 |
| Porous polyimide film, normal culturing, day 13 (Run 2) | 376 |
| Sheet cultured for 294 days (without gas phase subculturing) | 760 |
| Sheet cultured for 294 days (gas phase subcultured base sheet) | 709 |
| Sheet cultured for 56 days after gas phase subculturing (Upper) | 338 |
| Sheet cultured for 56 days after gas phase subculturing (Lower) | 266 |

Example 8

Freezing of Human Skin Fibroblasts and Substance Production

After adding 0.5 ml of cell culture medium to a 2 cm×2 cm square sterilized vessel, a 1.4 cm-square sterilized porous polyimide film was immersed therein with the A-surface of the mesh structure facing upward. After adding a suspension of $4 \times 10^4$ human skin fibroblasts per sheet onto the sheet in the medium, culturing was initiated in a $CO_2$ incubator. Cell culturing was continued with exchange of medium at a frequency of twice per week, and after cell culturing for 49 days, a CCK8 was used to measure the cell count, which was $9.1 \times 10^4$.

The cell-growing sheet was placed in a cryopreservation bag containing 3 ml of CELLBANKER, and after freezing to $-80°$ C. in a programmed freezer, by lowering the temperature $1°$ C. every 10 minutes, it was stored at $-80°$ C. for 24 hours and then transferred to liquid nitrogen. After 5 days, the bag was warmed to $37°$ C. to thaw the contents, 2 ml of medium was added, and the mixture was allowed to stand for 24 hours in an incubator. After 24 hours, 5 days, 8 days, 13 days, 21 days, 29 days and 35 days, a CCK8 was used to measure the cell count. After 24 hours, 8 days, 21 days and 35 days, the specific activity was found to be 34%, 91%, 105% and 152%, respectively. After culturing for 35 days, the amount of fibronectin production by the human skin fibroblasts growing on the same sheet was measured by ELISA. The results are shown in Table 10. For comparison, the fibronectin amount produced from two sheets cultured for 13 days with a porous polyimide film without freezing was also recorded. There was no damage by the freezing, and continuous substance production was confirmed.

TABLE 10

| Entry (days cultured and condition) | Fibronectin production per area (ng/cm²/day) |
| --- | --- |
| Porous polyimide film, normal culturing, day 13 (Run 1) | 480 |
| Porous polyimide film, normal culturing, day 13 (Run 2) | 376 |
| Sheet cultured for 35 days after freezing and thawing | 685 |

The invention claimed is:

1. A method of producing a substance using cells, the method including the steps of:
    applying the cells to a porous polyimide film,
    culturing the cells in the porous polyimide film to produce the substance by the cells, and
    recovering the substance,
    wherein the porous polyimide film has a three-layer structure consisting of an A-surface layer having a plurality of pores, a B-surface layer having a plurality of pores, and a macro-void layer sandwiched between the two surface layers,
    a mean pore size in the A-surface layer is smaller than a mean pore size in the B-surface layer, and
    the macro-void layer has a partition bonded to the A-surface layer and the B-surface layer, and a plurality of macro-voids surrounded by the partition, the A-surface layer, and the B-surface layer,
    wherein the substance is selected from the group consisting of proteins, glycoproteins and viruses.

2. A method of producing a substance using cells, the method including the steps of:
    applying the cells to a porous polyimide film,
    culturing the cells in the porous polyimide film to produce the substance by the cells, and
    recovering the substance,
    wherein the porous polyimide film has a three-layer structure consisting of an A-surface layer having a plurality of pores, a B-surface layer having a plurality of pores, and a macro-void layer sandwiched between the two surface layers,
    a mean pore size in the A-surface layer is smaller than a mean pore size in the B-surface layer, and
    the macro-void layer has a partition bonded to the A-surface layer and the B-surface layer, and a plurality of macro-voids surrounded by the partition, the A-surface layer, and the B-surface layer,
    wherein the cells are cultured under static culture conditions, or the cells are cultured under rotating culture or stirred conditions.

3. The method according to claim 1, wherein the cells are cultured in a continuous manner.

4. The method according to claim 3, including:
    setting a cell culturing apparatus in an incubator and culturing the cells, wherein
    the cell culturing apparatus includes:
    a culturing unit that houses one or more porous polyimide films to support cells, and that comprises a culture medium supply port and a culture medium discharge port, and
    a culture medium-supply unit comprising a culture medium housing vessel, a culture medium supply line, and a liquid conveyance pump that conveys the medium through the culture medium supply line, the first end of the culture medium supply line contacting the medium in the culture medium housing vessel, and the second end of the culture medium supply line being in communication with the culturing unit interior via the culture medium supply port of the culturing unit.

5. The method according to claim 4, wherein the cell culturing apparatus does not have an air supply port, an air discharge port and an oxygen permeation film.

6. The method according to claim 1, wherein the porous polyimide film comprises a polyimide obtained from a tetracarboxylic dianhydride and a diamine.

7. The method according to claim 6, wherein the porous polyimide film is a colored porous polyimide film obtained by forming a composition including a polyamic acid solution obtained from a tetracarboxylic dianhydride and a diamine, and a coloring precursor, and then heat treating it at $250°$ C. or higher.

8. The method according to claim 1, wherein the film thickness of the porous polyimide film is no greater than 75 μm.

9. The method according to claim 8, wherein the porous polyimide film is:
    i) folded,
    ii) wound into a roll,
    iii) connected as sheets or fragments by a filamentous structure, or
    iv) bound into a rope,
    and suspended or anchored in the cell culture medium in the cell culturing vessel.

10. The method according to claim 8, using two or more porous polyimide films layered either above and below or left and right in the cell culture medium.

11. The method according to claim 1, wherein the cells are transformed by genetic engineering technology so as to express a substance.

12. The method according to claim 11, wherein the cells are selected from the group consisting of animal cells, insect cells, plant cells, yeast cells and bacteria.

13. The method according to claim 12, wherein the animal cells are cells derived from an animal belonging to the subphylum Vertebrata.

14. The method according to claim 12, wherein the animal cells are selected from the group consisting of Chinese hamster ovary tissue-derived cells (CHO cells), African green monkey kidney-derived established cell lines (Vero cells), human hepatic cancer-derived cells (HepG2 cells), canine kidney epithelial cell-derived cell lines (MDCK cells) and human hepatic cancer tissue-derived established cell lines (huGK-14).

15. The method according to claim 14, wherein the bacteria are selected from the group consisting of lactic acid bacteria, *E. coli, Bacillus subtilis* and cyanobacteria.

\* \* \* \* \*